United States Patent
Tanaka et al.

(10) Patent No.: US 6,692,448 B2
(45) Date of Patent: Feb. 17, 2004

(54) ARTIFICIAL BONE TEMPLATE SELECTION SYSTEM, ARTIFICIAL BONE TEMPLATE DISPLAY SYSTEM, ARTIFICIAL BONE TEMPLATE STORAGE SYSTEM AND ARTIFICIAL BONE TEMPLATE RECORDING MEDIUM

(75) Inventors: Hiroshi Tanaka, Kaisei-machi (JP); Kazuo Shimura, Kaisei-machi (JP); Takeshi Ohkubo, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 0 days.

(21) Appl. No.: 09/954,005

(22) Filed: Sep. 18, 2001

(65) Prior Publication Data

US 2002/0055692 A1 May 9, 2002

(30) Foreign Application Priority Data

Sep. 18, 2000 (JP) .................................... 2000-281186
Sep. 18, 2000 (JP) .................................... 2000-281712
Sep. 18, 2000 (JP) .................................... 2000-281713

(51) Int. Cl.$^7$ ............................ A61B 5/103; A61B 5/117
(52) U.S. Cl. ...................................................... 600/587
(58) Field of Search .............................. 600/587, 590, 600/592, 594; 623/23.56, 16.11; 501/1; 523/116; 264/6, 430, 434, 482, 497, 628, 632

(56) References Cited

U.S. PATENT DOCUMENTS

| | | |
|---|---|---|
| 5,360,446 A | 11/1994 | Kennedy |
| 5,824,085 A | 10/1998 | Sahay et al. |
| 6,002,859 A | 12/1999 | DiGioia, III et al. |

FOREIGN PATENT DOCUMENTS

| | | | |
|---|---|---|---|
| EP | 0 574 099 A2 | 12/1993 | |
| EP | 0 411 155 B1 | * 5/1997 | ............ A61B/10/00 |

* cited by examiner

Primary Examiner—Max F. Hindenburg
Assistant Examiner—Brian Szmal
(74) Attorney, Agent, or Firm—Sughrue Mion, PLLC (57) ABSTRACT

An artificial bone template selection system includes a template data storage system in which template data representing a plurality of templates representing a plurality of artificial bones of different shapes is stored. A bone shape measuring system measures the shape of bone to be replaced by artificial bone on the basis of bone image data representing an image including the bone to be replaced by artificial bone. A prospective template selection system selects at least one template the shape of which substantially conforms to the shape of the bone to be replaced by artificial bone as measured by the bone shape measuring system out of the plurality of templates represented by the template data.

8 Claims, 9 Drawing Sheets

ARTIFICIAL BONE TEMPLATE SELECTION SYSTEM, ARTIFICIAL BONE TEMPLATE DISPLAY SYSTEM, ARTIFICIAL BONE TEMPLATE STORAGE SYSTEM AND ARTIFICIAL BONE TEMPLATE RECORDING MEDIUM

BACKGROUND OF THE INVENTION

1. Field of the Invention

This invention relates to an artificial bone template selection system which selects an artificial bone template suitable for the part of bone to be replaced by artificial bone out of a plurality of artificial bone templates prepared in advance. This invention further relates to an artificial bone template display system which displays artificial bone templates which have been prepared, an artificial bone template storage system which stores a plurality of artificial bone templates prepared in advance, and an artificial bone template recording medium for recording thereon artificial bone templates.

2. Description of the Related Art

In the orthopedic surgery, the oral surgery and the like, when a patient loses a part of a bone due to disease or accident or by a surgical removal as treatment for malignant tumor, the lost part of the bone has been replaced by his or her own bone of another part.

Recently, artificial bone (artificial hard tissue) of stainless steel, cobalt-chrome series alloy, metal such as titanium, aluminum or zirconium, oxide of these metals, ceramic such as apatite, or composite material of these materials has been put into practical use as substitution for the lost part of the bone.

Artificial bone which is to be embedded in place of the lost part of the bone is produced on the basis of a standard model which is selected, on the basis of the shape of the part to be replaced by the artificial bone, out of a plurality of standard models which have been prepared, in advance, in different shapes.

Conventionally, the standard models are stored in the form of real templates representing the contours of the standard models (e.g., templates formed of transparent plastic sheets), and the real templates are superposed on an image of the lost part of the bone in sequence and whether each of the templates conforms to the lost part of the bone is visually checked.

However, since the standard models are prepared at intervals of 1 mm of the diameter of the bone head (the head of the bone) or the length of the bone shaft or the bone holder and at intervals of 1° of the angle between the bone shaft and the bone holder, the number of the standard models or the real templates is numerous, and accordingly, to select one template in the conventional way is a time-consuming and labor-consuming process.

Further, since being manually superposed on the image of the lost part of the bone in a limited time interval, each template cannot be accurately aligned with the image of the lost part and an optimal standard model or template cannot be constantly selected.

Further, since numerous templates must be kept at hand, management of the templates is troublesome.

SUMMARY OF THE INVENTION

In view of the foregoing observations and description, the primary object of the present invention is to provide an artificial bone template selection system which can efficiently select an artificial bone template suitable for the part of bone to be replaced by artificial bone out of a plurality of artificial bone templates prepared in advance.

Another object of the present invention is to provide an artificial bone template display system which displays artificial bone templates in such a manner that a suitable template can be selected in a shorter time, and management of templates can be facilitated.

Still another object of the present invention is to provide a template data storage system which stores electronic data on the templates in such a manner that a suitable template can be selected in a shorter time.

Still another object of the present invention is to provide a computer-readable recording medium which stores electronic data on the templates in such a manner that a suitable template can be selected in a shorter time.

In accordance with a first aspect of the present invention, there is provided an artificial bone template selection system comprising a template data storage means in which template data representing a plurality of templates representing a plurality of artificial bones of different shapes is stored, a bone shape measuring means which measures the shape of bone to be replaced by artificial bone on the basis of bone image data representing an image including the bone to be replaced by artificial bone, and a prospective template selection means which selects, as a prospective template, at least one template the shape of which substantially conforms to the shape of the bone to be replaced by artificial bone as measured by the bone shape measuring means out of the plurality of templates represented by the template data.

Preferably, there are provided a display means which displays the bone image representing the shape of the bone to be replaced by the artificial bone and an image of the prospective template(s) selected by the prospective template selection means and a display control means which causes the display means to display the bone image and the image of the prospective template superposed one on another.

In accordance with a second aspect of the present invention, there is provided an artificial bone template selection system comprising a template data storage means in which template data representing a plurality of templates representing a plurality of artificial bones of different shapes is stored, a bone image display means which displays the bone image representing the shape of the bone to be replaced by the artificial bone, a feature point designating means which designates on the bone image displayed by the bone image display means a feature point representing the shape of the bone, a bone shape specifying means which specifies the shape of the bone on the basis of the feature point designated by the feature point designating means, and a prospective template selection means which selects, as a prospective template, at least one template the shape of which substantially conforms to the shape of the bone specified by the bone shape specifying means out of the plurality of templates represented by the template data.

The artificial bone template selection system in accordance with the second aspect of the present invention differs from that of the first aspect of the present invention in that the former specifies the shape of the bone to be replaced by the artificial bone on the basis of a feature point designated on the image of the bone displayed by the display means whereas the latter specifies the shape of the bone to be replaced by the artificial bone on the basis of the bone image data.

As the feature point representing the shape of the bone, the center of the bone head, the edge of the bone head, the longitudinal ends of the bone shaft and the bone holder, and the like may be used. By designating the center and the edge of the bone head, the diameter of the bone head can be specified, and by designating the longitudinal ends of the bone shaft and the bone holder, the lengths of the bone shaft and the bone holder and the angle therebetween can be specified. Further, when the diameter of the bone head, the lengths of the bone shaft and the bone holder and the angle therebetween are specified, the overall shape of the bone can be specified.

Preferably there are provided a display means which displays an image of the prospective template(s) selected by the prospective template selection means and a display control means which causes the display means to display the bone image and the image of the prospective template superposed one on another.

When the bone image and the image of the prospective template are displayed superposed one on another in the artificial bone template selection system in accordance with the first or second aspect of the present invention, it is preferred that an image processing means which carries out image processing on at least one of the images displayed by the display means so that their shapes can be more clearly discriminated be provided, and the image processed by the image processing means is displayed in the processed condition.

The expression "so that their shapes can be more clearly discriminated" means "so that discrimination between the shapes of the prospective templates is facilitated" (in the case where a plurality of prospective templates are selected) as well "so that discrimination between the shapes of the prospective template and the bone image is facilitated".

In the artificial bone template selection system in accordance with the first or second aspect of the present invention, it is preferred that an order information output means which outputs, for instance, a data file on information for ordering artificial bone corresponding to the template selected by the prospective template selection means, e.g., maker, model number, number, delivery time, place of delivery, and the like, be provided.

The information for ordering the artificial bone need not be for all the prospective templates selected by the prospective template selection means but may be for only a final template which is finally selected from the prospective templates selected by the prospective template selection means.

The template data used in the artificial bone template selection system in accordance with the first or second aspect of the present invention is preferably prepared not only for storing images of the templates as electronic data but also for facilitating retrieval and shape matching. For example, the template data preferably comprises an image file in which a plurality of pieces of image data each representing one template are recorded and a shape data file in which a plurality of pieces of shape data (e.g., vector data) each representing a feature of the shape of a template are recorded in correlation with the image data for the template.

The template data comprising the image data and the shape data may be provided recorded on a computer-readable recording medium.

In the artificial bone template selection system in accordance with the first aspect of the present invention, one or more prospective templates, the shape of which substantially conforms to the shape of the bone to be replaced, can be automatically selected without visually checking whether each of the templates conforms to the bone or manually superposing each of the templates on the image of bone, whereby one or more standard artificial bone can be selected easily in a short time.

Further, when the bone image and the image of the prospective template are displayed superposed one on another, whether the prospective template is really suitable for the bone to be replaced can be judged observing the superposed image. In this case, since the number of the prospective templates is limited by the automatic selection, a template most optimal to the bone can be easily and quickly selected.

In the artificial bone template selection system in accordance with the second aspect of the present invention, one or more prospective templates, the shape of which substantially conforms to the shape of the bone to be replaced, can be automatically selected even if the bone is too complicated in shape for the artificial bone template selection system in accordance with the first aspect of the present invention to select a template suitable for the bone.

As in the artificial bone selection system in accordance with the first aspect of the present invention, when the bone image and the image of the prospective template are displayed superposed one on another, whether the prospective template is really suitable for the bone to be replaced can be judged observing the superposed image. In this case, since the number of the prospective templates is limited by the automatic selection, a template most optimal to the bone can be easily and quickly selected.

Further, in both the artificial bone template selection systems in accordance with the first and second aspects of the present invention, since a template data storage means in which template data representing a plurality of templates representing a plurality of artificial bones of different shapes is stored in the form of electronic data is used, management of the templates becomes unnecessary.

Further, in both the artificial bone template selection systems in accordance with the first and second aspects of the present invention, when an image processing means which carries out image processing on at least one of the images displayed by the display means so that their shapes can be more clearly discriminated is provided and the image processed by the image processing means is displayed in the processed condition, the bone image and the image of the prospective template can be easily discriminated from each other, which permits the operator to more accurately locate the images with respect to each other in a short time. Further, a template most optimal to the bone can be easily and quickly selected, and at the same time, relative position between the images can be more finely adjusted, whereby most optimal template can be surely selected.

Further, when the artificial bone template system is provided with an order information output means which outputs, information for ordering artificial bone corresponding to the template selected by the prospective template selection means, an automatic artificial bone order system which automatically orders artificial bone as soon as the prospective template selection processing can be realized. When the system is incorporated in a network such as using the internet, the user such as a doctor, a medical engineer and the like can directly trade with a maker or an agency without intervening therebetween a broker.

DESCRIPTION OF THE PREFERRED EMBODIMENTS

Figure 1:
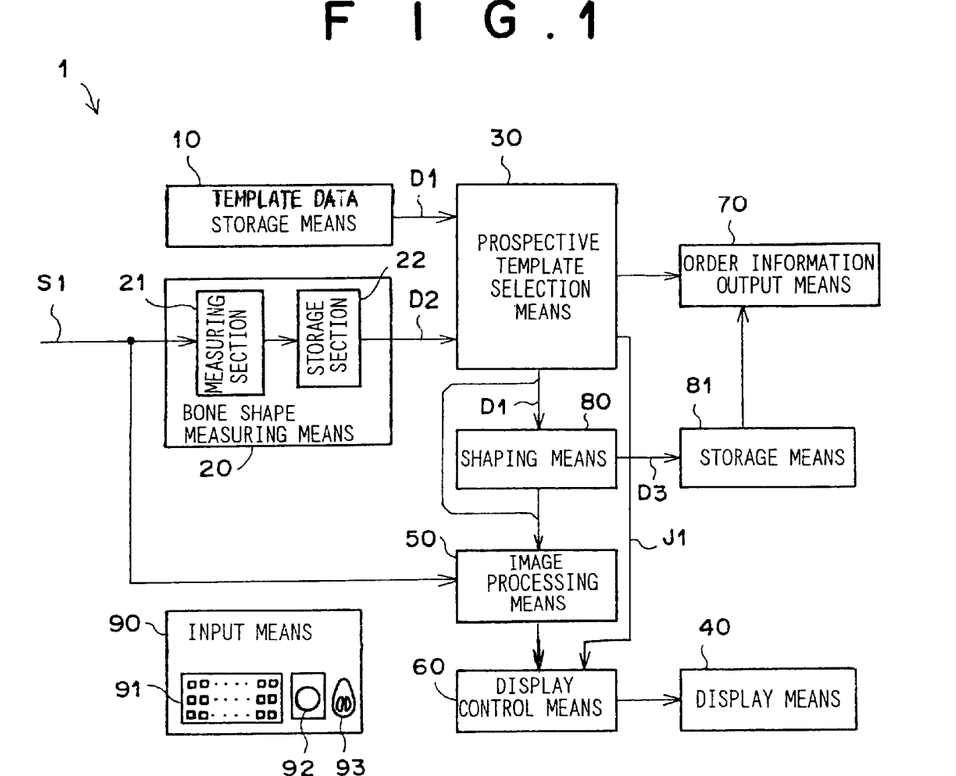
FIG. 1 is a block diagram showing an artificial bone template selection system in accordance with a first embodiment of the present invention.

In FIG. 1, an artificial bone template selection system 1 in accordance with a first embodiment of the present invention comprises a template data storage means 10 in which template data representing a plurality of templates representing a plurality of artificial bones of different shapes is stored, a bone shape measuring means 20 which measures the shape of bone to be replaced by artificial bone on the basis of bone image data representing an image including the bone to be replaced by artificial bone, a prospective template selection means 30 which selects, as a prospective template, at least one template the shape of which substantially conforms to the shape of the bone to be replaced by artificial bone as measured by the bone shape measuring means 20 out of the plurality of templates represented by the template data, a display means 40 (e.g., a CRT or a liquid crystal panel) which displays the bone image representing the shape of the bone to be replaced by the artificial bone and an image of the prospective template(s) selected by the prospective template selection means 30, an image processing means 50 which carries out image processing on the images displayed by the display means so that their shapes can be more clearly discriminated from each other, a display control means 60 which causes the display means 40 to display the bone image and the image of the prospective template superposed one on another on the basis of the processed image data, and an order information output means 70 which outputs order information for ordering artificial bone for replacing the bone.

The artificial bone template selection system 1 further comprises a shaping means 80 which deforms, on the screen of the display means 40, the shape of a standard template represented by template data read out from the template data storage means 10, a storage means 81 which stores difference data D3 representing the difference in shape between the standard template and a deformed template obtained by deforming the standard template by the shaping means 80, and an input means 90 (consisting of a keyboard 91, a dial 92, a mouse 93 and the like) for inputting data for selecting a more desirable template out of prospective templates and/or for carrying out various operations.

Figure 2:
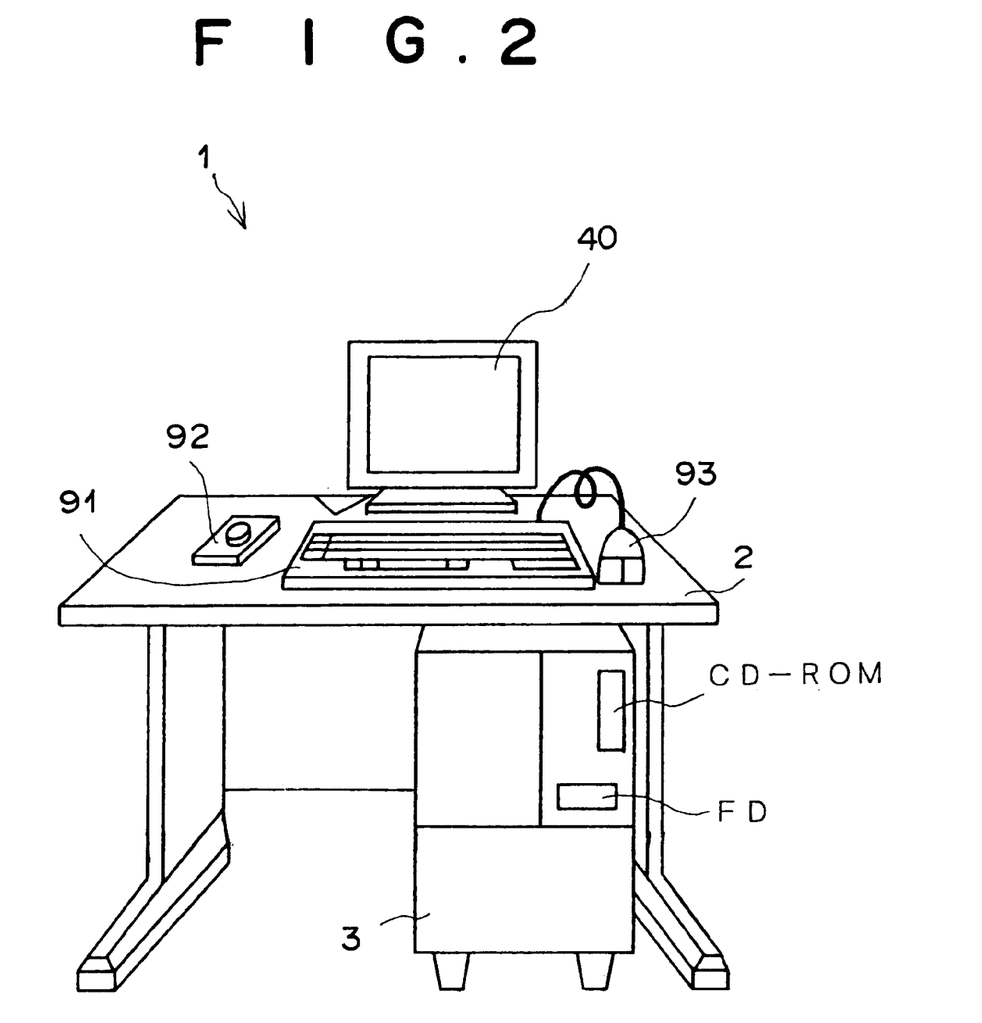
FIG. 2 is a schematic view showing an appearance of the artificial bone template selection system shown in FIG. 1.

As shown in FIG. 2, the display means 40, the input means 90 and the like are placed on a table 2, and the template data storage means 10, the bone shape measuring means 20 and the like are contained in a body 3 under the table 2.

The template data storage means 10 comprises, for instance, a magnetic recording device such as a hard disc which reads out template data from a computer-readable portable recording medium such as a CD-ROM or a MO and temporarily stores the template data read out. When the speed of the selection (retrieval) to be described later does not involve a problem, the template data may be read out from the computer-readable portable recording medium such as a CD-ROM or a MO on the spot.

The template data comprises an image file in which a plurality of pieces of image data each representing one template are recorded and a shape data file in which a plurality of pieces of template shape data D1 each representing a feature of the shape of a template are recorded in correlation with the image data for the template. The image file includes, in addition to life-size images of the standard templates, thumbnail images (scale-down images) of the standard templates (e.g., reduced ⅛ by ⅛).

By storing template images in the form of electronic data, whether each template conforms in shape to the bone to be replaced can be checked on the basis of electronic data and the necessity of keeping numerous templates at hand and managing the templates can be eliminated.

In this particular embodiment, vector data representing a geometrical feature is employed as the shape data D1. In the case of a femur, the diameter of the bone head, the length of the bone shaft, the length of the bone holder between the bone head and the bone shaft and/or the angle between the bone shaft and the bone holder can be employed as the vector data. With this arrangement, a database for facilitating retrieval and shape matching can be obtained.

The bone shape measuring means 20 comprises a measuring section 21 which measures the shape of the bone to be replaced on the basis of the image data S1, and a storage section 22 which stores bone shape data D2 representing the shape of the bone measured by the measuring section 21.

The prospective template selection means 30 carries out selection (retrieval) for selecting a standard template, which conforms to the shape of the bone to be replaced, on the basis of the bone shape data D2 obtained by measuring the bone (read out from the storage section 22) and the template shape data D1 read out from the template data storage means 10.

The image processing means 50 carries out image processing for facilitating discrimination between the shape of the template and the shape of the bone. For example, the image processing means 50 carries out image processing, during or after selection of the standard template, for displaying the edge of the bone and/or the template only in line, shading the image, displaying contour lines, displaying the overall shapes the bone and/or the template in a wire frame fashion or enhancing the edge of one of the bone and the template.

The display control means 60 sets layout of the frame of the display means 40 so that a template display area, where a list of prospective templates automatically selected by the prospective template selection means 30 and/or thumbnail images of the prospective templates is displayed and a bone image display area, where an image of the bone is displayed, are provided side by side. Further, the display control means 60 causes the display means 40 to display the image of the bone and the image of the template (the processed image, when it has been processed by the image processing means 50) in the template display area superposed one on another.

In the superposed display, all the prospective templates may be automatically located to be superposed on the image of the bone or only one or more of the prospective templates selected by the operator out of the prospective templates automatically selected by the prospective template selection means 30 may be superposed on the image of the bone. In the latter case, the prospective template(s) may be located under the instruction of the operator.

By thus setting the template display area and the bone image display area, the image of the bone and the list of the prospective templates (with the thumbnail images of the prospective templates) can be displayed simultaneously, and a final most optimal template can be selected at high efficiency out of a plurality of prospective templates automatically selected by the prospective template selection means 30.

Operation of the artificial bone template selection system 1 of this embodiment will be described, hereinbelow.

It is consumed here that a femur 9 (FIG. 3) is to be replaced by artificial bone, and a radiation image (CR image) including the image of the femur 9 is taken by a CR (computed radiography) system. That is, X-rays are projected through an object onto an imaging plate comprising stimulable phosphor so that a radiation image of the object is recorded on the imaging plate as a pattern of stored radiation energy. Then the radiation image recorded on the imaging plate is read out and bone image data S1 is obtained. The bone image data S1 is input into the artificial bone template selection system 1 of this embodiment.

Figure 4:
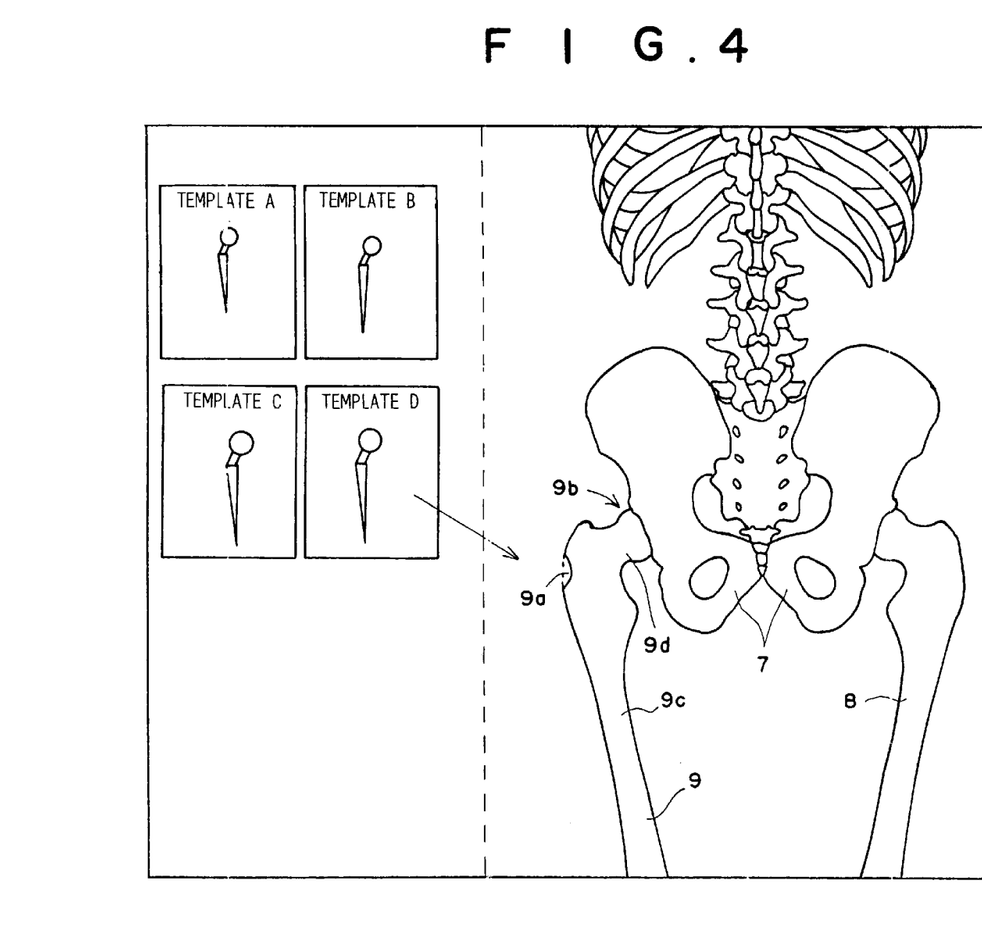
FIG. 4 is a view showing an example of the frame on the basis of which the template selection processing is carried out.

The display control means 60 causes the display means 40 to display a femur 9 with a lost part 9*a* together with bones 7 and 8 around the femur 9 in the bone image display area on the basis of the bone image data S1 as shown in FIG. 4.

Figure 3:
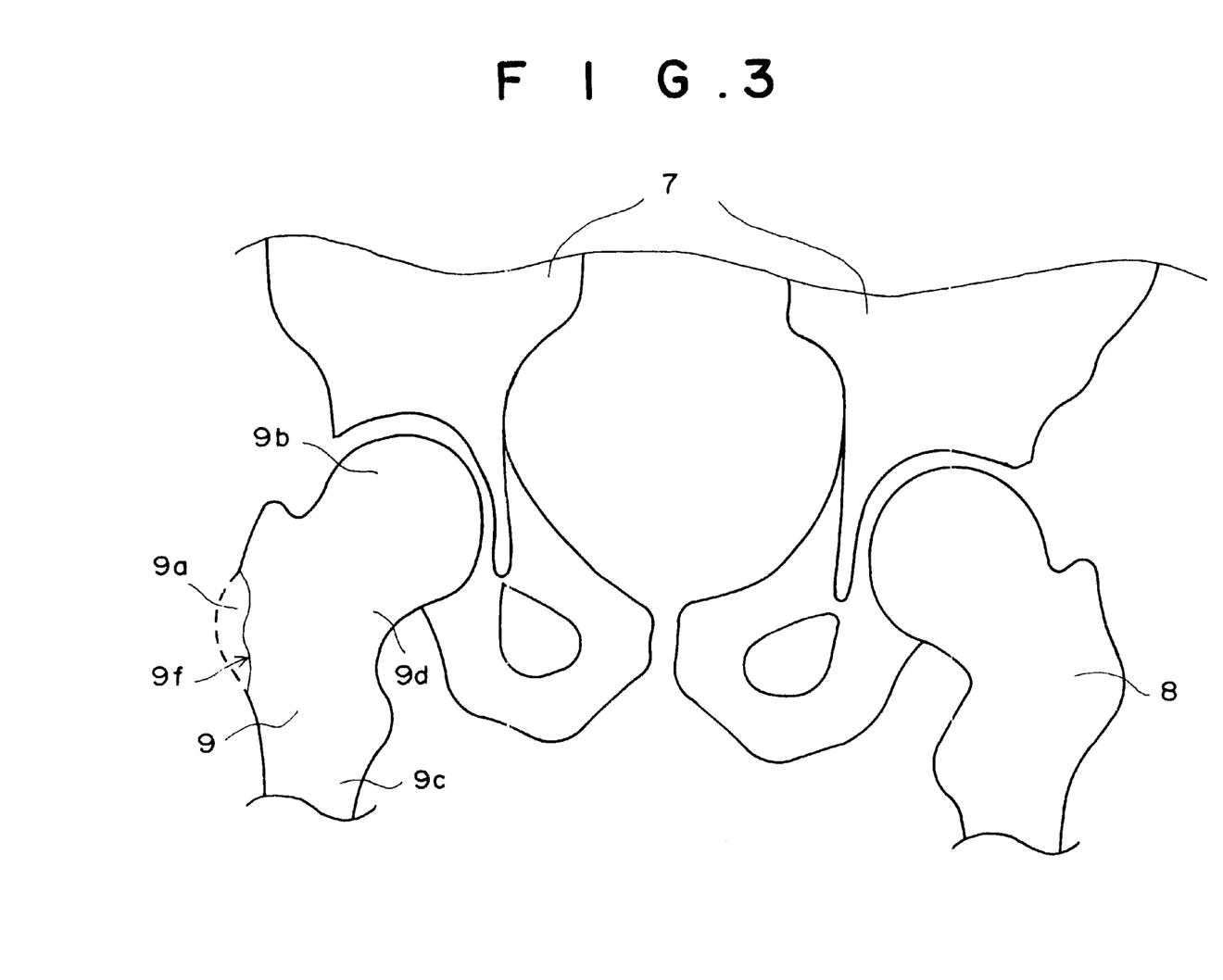
FIG. 3 is an enlarged view of a part including a femur as a bone to be replaced.

The bone image data S1 is input also into the measuring section 21 of the bone image measuring system 21. The measuring section 21 extracts the edge of the femur 9 with the lost part 9*a* by a known method and stores bone shape data representing the outer shape of the femur 9 in the storage section 22. The bone shape data D2 is in the same format as the template shape data D1 stored in the template data storage means 10. In this particular embodiment, since the template shape data D1 is vector data, the measuring section 21 obtains vector data representing the diameter of the bone head 9*b*, the length of the bone shaft 9*c*, the length the bone holder 9*d* and/or the angle between the bone shaft 9*c* and the bone holder 9*d* and stores the vector data in the storage section 22 as the bone shape data D2.

The information specifying the bone 9 with the lost part 9*a* to be replaced by artificial bone may be extracted from a menu code attached to the bone image data S1 or may be specified by the operator designating a point with the mouse 93 on the frame of the display means 40.

Thereafter, the prospective template selection means 30 reads the template shape data D1 of templates for a femur from the template data storage means 10, and selects one or more templates whose outer shape conforms to the contour of the femur 9 of the patient on the basis of the bone image data S1. The selection may be based on a pattern matching between the two pieces of image data in a raster form. However, it is preferred that the selection be carried out on the basis of comparison between the template shape data D1 and the bone shape data D2. That is, since the template shape data D1 and the bone shape data D2 are both vector data representing the diameter of the bone head 9*b*, the length of the bone shaft 9*c*, the length the bone holder 9*d* and/or the angle between the bone shaft 9*c* and the bone holder 9*d*, the selection (retrieval) can be done in a shorter time as compared with when the selection is done by simple pattern matching on the raster data.

The prospective template selection means 30 determines whether each of the standard templates for a femur conforms to the femur 9 with the lost part 9*a*, and automatically selects one or more of the standard templates whose difference from the affected femur 9 is within a predetermined range. When there is no standard template whose difference from the affected femur 9 is within the predetermined range, the prospective template selection means 30 selects one or more of the standard templates close to the predetermined range. In this manner, the prospective template selection means 30 selects at least one standard template as a prospective template.

The prospective template selection means 30 inputs into the display control means 60 information J1 on the prospective template(s) selected. The display control means 60 causes the display means 40 to display the numbers of the prospective templates selected (e.g., template A to template D) together with the thumbnail images thereof in the template image display area. It is preferred that the thumbnail images be read out from the template data storage means 10. When the thumbnail images are not prepared in advance, they are obtained by reducing the original image.

In addition to the numbers and the thumbnail images of the prospective templates, information on the maker, model number and the like of the artificial bone represented by the prospective templates may be read out from the template data storage means 10 and displayed in the template display area.

Further, the list of the prospective templates (e.g., the number of the prospective templates, the model number of the same, and the like) may be output on a recording medium such as paper as well being displayed by the display means 40.

The operator or the doctor determines whether the automatic selection is satisfactory on the basis of the list and/or the thumbnail images of the selected prospective templates. When the automatic selection is satisfactory, the operator inputs the effect that the automatic selection is satisfactory into the artificial bone template selection system 1.

It is possible to check whether the automatic selection is satisfactory by superposing the prospective templates (limited in number) on the CR film image of the affected bone 9. Also in this case, since the number of the prospective templates has been reduced by the automatic selection, the checking can be done in a shorter time.

When it is determined that the automatic selection is unsatisfactory or when it is required to further reduce the number of the prospective templates (e.g., to 1), the bone image data S1 is analyzed in further detail, and templates which further conform to the bone in shape are selected out of the prospective templates. This selection may be done in the following manner by operating the keyboard 91, the mouse 93, the dial 92 and the like viewing the screen of the display means 40.

That is, the display means 40 is caused to display a template selection frame such as shown in FIG. 4. Then, the operator selects one of the templates in the list of prospective templates (or the thumbnail images thereof) displayed in the template display area on the screen of the display means 40. This selection may be done by pointing with the mouse 93 the template to be selected or by inputting the number of the template to be selected through the keyboard 91.

When one of the prospective templates is selected, the prospective template selection means 30 reads out image data representing the selected prospective template in an original size from the template data storage means 10 and inputs it into the image processing means 50. Then the display control means 60 causes the display means 40 to display an image of the selected prospective template in the original size.

Thereafter, the image of the selected prospective image in the original size is moved to the image of the bone 9 to be replaced by artificial bone and superposed thereon. This operation of superposing the image of the selected prospective image in the original size on the image of the bone 9 to be replaced is preferably done by drag and drop with the mouse 93.

At this time, it is preferred that image processing means 50 carries out image processing for facilitating discrimination between the shape of the prospective template and the shape of the bone. For example, the image processing means 50 carries out image processing for enhancing edges of the images, shading the one of the images, displaying the edge of the bone and/or the template only in line (solid line or dotted line), displaying the overall shapes the bone and/or the template in a wire frame fashion or displaying the images in different colors. If required, the images may be displayed in an enlarged size so that whether the selected prospective template well conforms to the bone to be replaced can be visually checked more easily and superposing accuracy is increased.

The image of the selected prospective template moved to the image of the bone is finely moved up and down and right and left and finely rotated so that the image of the selected prospective template conforms to the image of the bone to be replaced in position, inclination and the like. These operation is preferably carried out by designating a translating movement mode or a rotational movement mode by the keyboard 91 and moving the image of the selected prospective template by a distance or an angle corresponding to the amount of rotation of the dial 92.

This process is repeated while changing the prospective templates and selecting a prospective template most suitable for the bone 9 to be replaced. In this manner, information on a final prospective template is stored in the storage means 81.

When the bone 9 is not to be replaced in whole but artificial bone is embedded only in place of the lost part 9a of the femur 9, geometrical data such as coordinates of the edge 9f (FIG. 3) of the lost part 9a of the femur 9 for defining the lost part 9a on the prospective templates is also stored in the storage means 81.

If desired, the template shape data D1 on the final prospective template is input into the shaping means 80 and the prospective template is slightly enlarged or reduced in whole or a part of the template is finely deformed so that the final prospective template is adjusted to a shape which strictly conforms to the shape of the bone 9 to be replaced. Then difference data D3 representing the difference of the shape of the final prospective template after the adjustment from that before the adjustment is stored in the storage means 80.

The fine deformation of only a part of the final prospective template is preferably carried out by first designating the part to be deformed with the mouse 93, designating a translating movement mode or a rotational movement mode by the keyboard 91 and then deforming the designated part by a value corresponding to the amount of rotation of the dial 92. Such a local deformation can be carried out by changing coordinate parameters and/or function parameters which define the shape of the template and are obtained on the basis of the template shape data D1.

The amount of movement of the image of the template or the amount of change of the parameters when the image of the template is to be moved or the template is to be partly deformed can be set also by inputting numerical values through the keyboard 91.

The operation of deforming the template or moving the image of the template can be easily carried out when the image of the bone to be replaced and the image of the template are displayed superposed one on another. Further since such operation is carried out only on templates which have been automatically selected on the basis of the image data, selection of a suitable template can be carried out in a shorter time.

Then an order file for ordering artificial bone corresponding to the template thus selected, e.g., maker model number (template number), number of the templates, delivery time, place of delivery, the difference data D3, and the like, is made by the order information output means 70 and the order file is sent to a maker or an agency.

Figure 5:
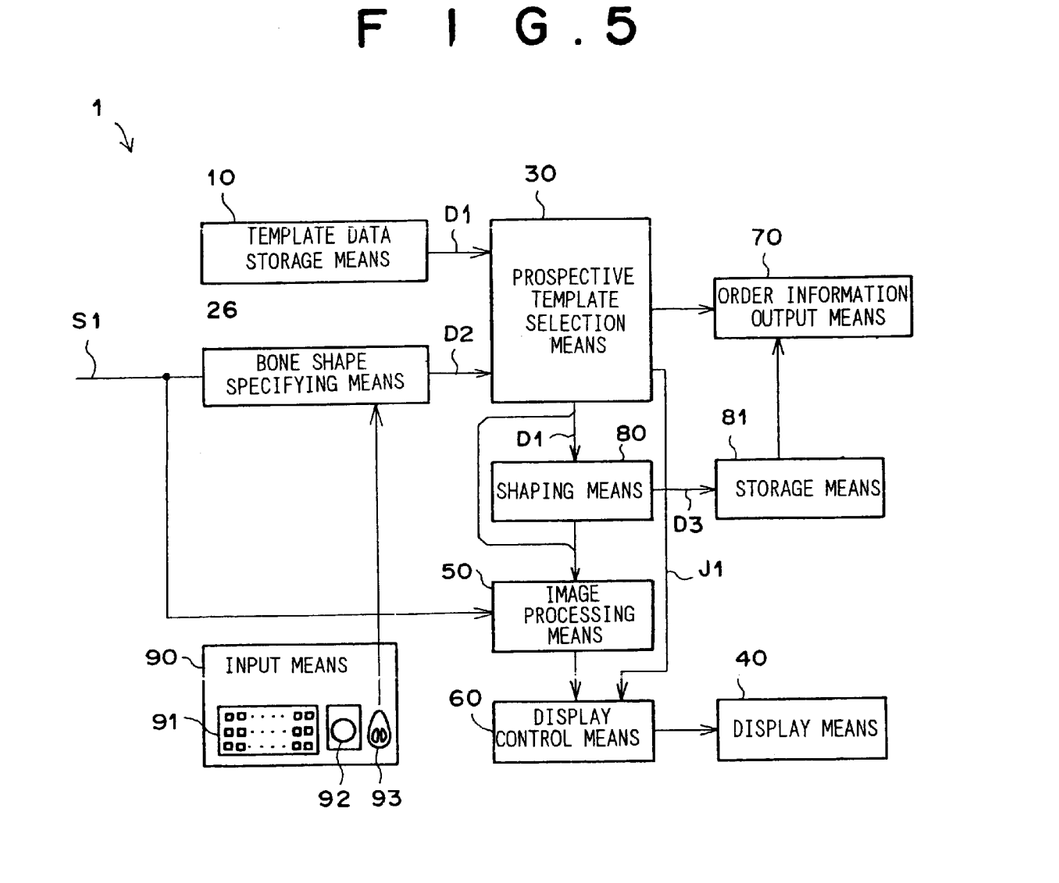
FIG. 5 is a block diagram showing an artificial bone template selection system in accordance with a second embodiment of the present invention.
Figure 6:
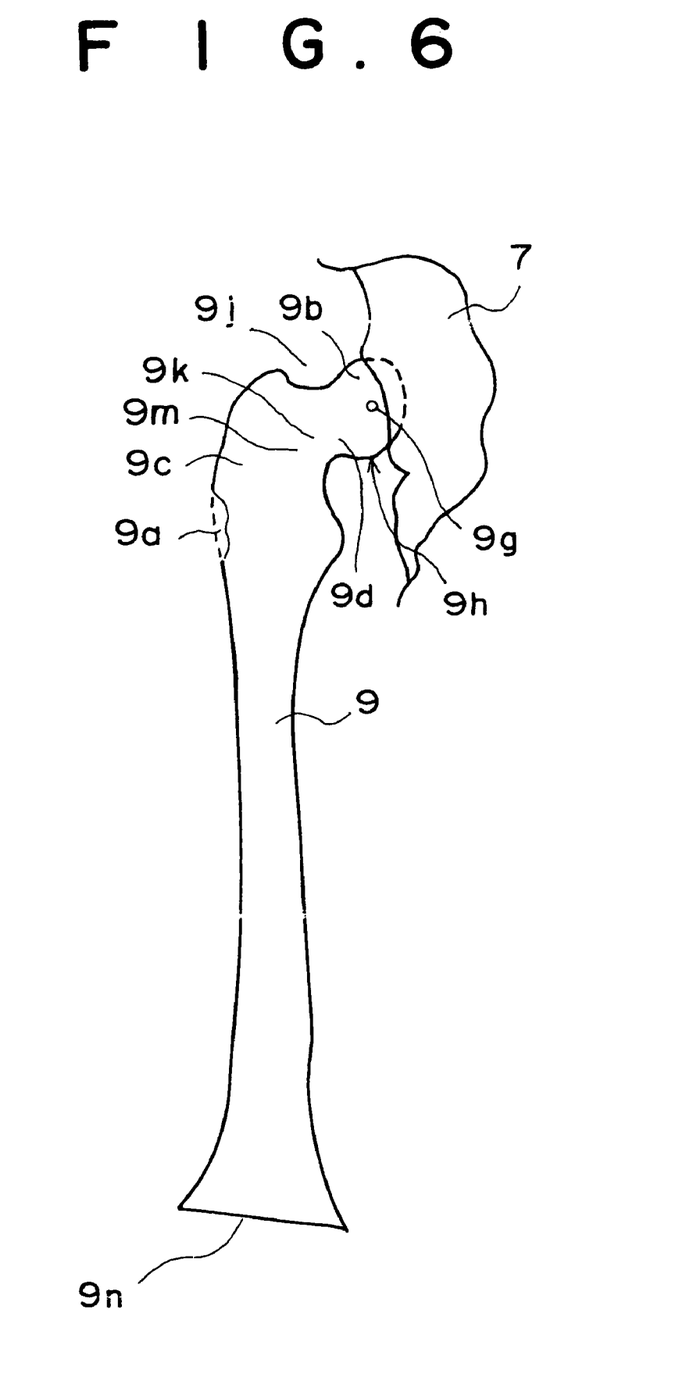
FIG. 6 is a view for illustrating a method of designating on the displayed bone image a feature point representing the shape of the bone.

An artificial bone template selection system in accordance with a second embodiment of the present invention will be described with reference to FIGS. 5 and 6, hereinbelow.

In the artificial bone template selection system in accordance with the second embodiment of the present invention, feature points are designated on the image of the bone to be replaced and the bone shape data D2 representing the shape of the bone to be replaced is obtained on the basis of the designated feature points.

In this embodiment, as the means for designating the feature points on the image displayed by the display means 40, a pointing device such as a mouse 93 is employed, and a bone shape specifying means 26, which obtains as vector data the bone shape data D2 on the basis of the designated feature points, is provided in place of the bone shape measuring means 20 employed in the first embodiment.

In the artificial bone template selection system 1 of the second embodiment, the operator designates feature points on the image of the bone displayed by the display means 40. This designation may be carried out, for instance, by designating the diameter of the bone head 9b by pointing the center 9g and the edge 9h of the bone head 9b, designating the length of the bone shaft 9c by pointing the longitudinal ends 9m and 9n, designating the length of the bone holder 9d by pointing the longitudinal ends 9j and 9k and designating the angle θ between the bone shaft 9c and the bone holder 9d by pointing the longitudinal ends 9m and 9n of the bone shaft 9c and the longitudinal ends 9j and 9k of the bone holder 9d. The bone shape specifying means 26 obtains as vector data the bone shape data D2 on the basis of the designated feature points. The prospective template selection means 30 selects at least one of the standard templates as a prospective template in the same manner as that employed in the first embodiment.

Since pointing the feature points with the mouse 93 can be intuitively done observing the image of the bone displayed on the display means 40, the shape of the bone can be suitably specified even if the bone is complicated in shape and selection of the artificial bone template can be automatically carried out.

Though preferred embodiments of the present invention are described above, the present invention need not be limited to the embodiments described.

For example, though, in the embodiments described above, the bone shape data D2 is obtained as vector data and whether the template conforms in shape to the bone to be replaced is checked by the use of the bone shape data D2 in the form of vector data and the template shape data D1 also in the form of vector data, whether the template conforms in shape to the bone to be replaced is checked by pattern matching by the use of raster data representing the bone to be replaced and raster data representing the standard template.

Further, after prospective templates are automatically selected by the prospective template selection means 30, images of all the prospective templates may be superposed on the image of the bone to be replaced by automatic alignment processing and which of the prospective templates is the best may be determined viewing the superposed image.

In this case, when the prospective template selection means 30 selects a plurality of prospective templates, it is preferred that the contours of the image of the bone and the prospective templates be displayed in a wire frame fashion and the wire frames for the respective image be displayed in different colors.

Further, when the prospective template selection means 30 selects a plurality of prospective templates, it is possible to set a display area for each prospective template and display a superposed image in each display area.

Prospective templates can be clearly discriminated from each other by the use of such a layout.

As the image data S1 representing an image including the bone to be replaced by artificial bone, image data obtained by reading out an image on X-ray film by an image scanner, cross-sectional image data obtained by CT or MRI, three-dimensional image data obtained by reconfiguration, or the like may be employed in place of a radiation image read by a CR system.

The template data storage means 10 will be described in more detail with reference to FIGS. 7 to 9B, hereinbelow.

Figure 7:
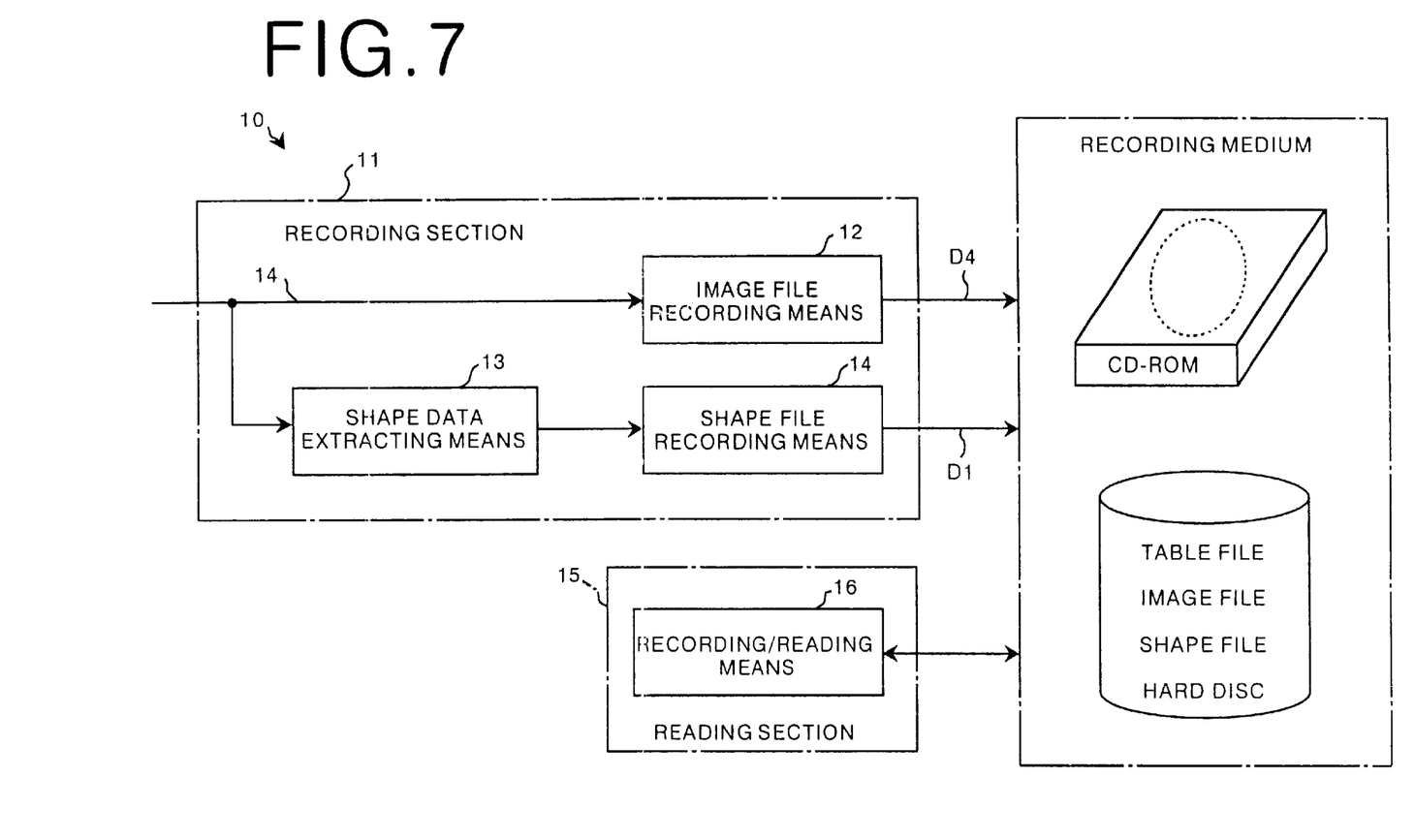
FIG. 7 is a block diagram showing in detail the template data storage means.

As shown in FIG. 7, the template data storage means 10 comprises a recording section 11 which records data on a predetermined recording medium and a recording section 15 which reads out data from the recording medium. The recording section 11 comprises an image file recording means 12 which records a plurality of pieces of template image data D4, each piece representing an image of one template, in an image file, a shape data extracting means 13 which extracts a plurality of pieces of template shape data D1, each representing a feature of the shape of a template, on the basis of template image data D4 on each template, and a shape file recording means 14 in which the pieces of template shape data D1 extracted by the shape data extracting means 13 are recorded in correlation with the template image data for each template.

The recording medium employed in the recording section 11 or the reading section 15 may be a computer-readable portable recording medium such as a CD-ROM, CD-RAM, DVD-ROM, DVD-RAM or a MO as well as a fixed type magnetic recording medium such as a hard disc.

The reading section 15 is provided with a recording/reading means 16 which reads out template data recorded on a portable recording medium such as a CD-ROM, MO or the like and temporarily stores the template shape data read out from the portable recording medium in a recording medium such as a hard disc.

When a hard disc is employed as the recording medium in the recording section 11, the processing of reading out the template shape data becomes unnecessary. When the speed of the selection (retrieval) to be described later does not involve a problem, the template data may be read out from the computer-readable portable recording medium such as a CD-ROM or a MO each time required.

The recording section 11 and the reading section 15 may comprise, for instance, a computer system using a CPU.

Figure 8:
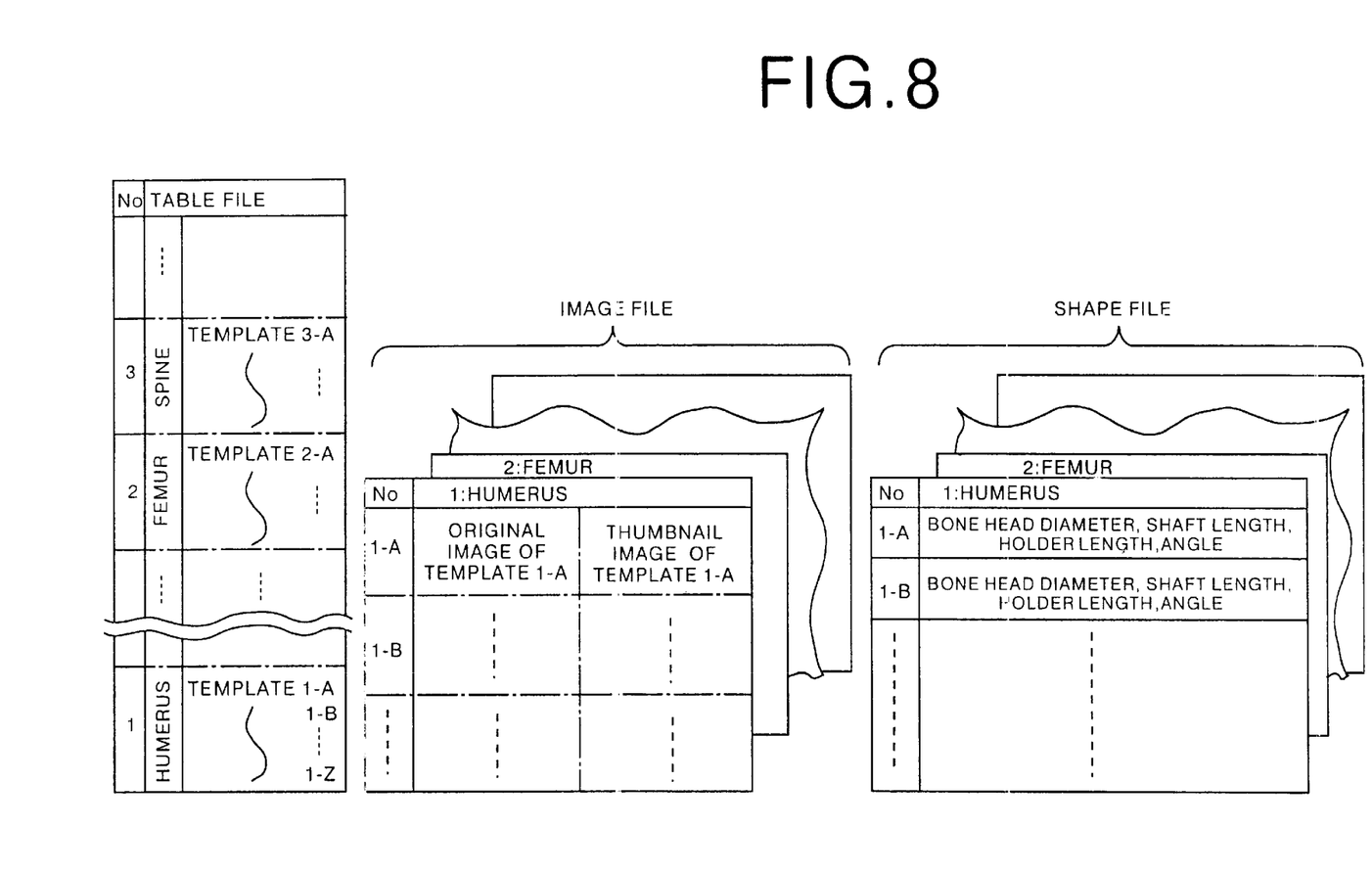
FIG. 8 is a view showing an example of the structure of template data.

As shown in FIG. 8, the template data comprises an image file in which a plurality of pieces of image data D4 each representing one template are recorded and a shape file in which a plurality of pieces of shape data D1 each representing a feature of the shape of a template are recorded in correlation with the image data D1 for the template. It is preferred that the image file includes, in addition to life-size images of the standard templates, thumbnail images (scale-down images) of the standard templates (e.g., reduced ⅛ by ⅛).

Further, the template data is provided with a table file for taking a correspondence between each standard template and the file number of the image file and the shape file for the standard template. Further in order to facilitate, the image files and the shape files are grouped by part, e.g., humerus, knee joint and the like.

As the template shape data D1, vector data representing the diameter of the bone head, the length of the bone shaft, the length of the bone holder between the bone head and the bone shaft and/or the angle between the bone shaft and the bone holder can be employed. With this arrangement, not only the images of templates are simply stored in the form of electronic data but also a database for facilitating retrieval and shape matching can be obtained.

Creation of a database on the template data will be described, hereinbelow.

The image file recording means 12 makes an image file in which a plurality of sets of template image data D4 obtained by reading images of a plurality of standard templates with an image scanner or the like, and stores the image file in the recording medium such as a hard disc or a CD-ROM. It is preferred that thumbnail images of each standard template be included in the image file in addition to the original image of the standard template as described before. It is further preferred that the image data be compressed by a known image compression method such as JPEG.

The shape data extracting means 13 measures the contour shape of each standard template by analyzing the image data D4 on the template. Then the shape data extracting means 13 obtains vector data representing the feature of the contour shape of each template and inputs the vector data into the shape file recording means 14 as the template shape data D1. For example, in the case of templates for the femur, sets of data respectively representing the diameter of the bone head, the length of the bone shaft, the angle between the bone shaft and the bone holder, the length of the bone holder, and the like are taken as the vector data.

It is possible to eliminate the shape data extracting means 13. In this case, the operator manually measures the vector data of each standard template with a scale or the like, and inputs the data thus obtained into the template data storage means 10 through the keyboard 91.

The shape file recording means 14 makes a table file which correlates the template shape data D1 and the template image data D4 with each other while grouping them by part, and records the table file and the shape file thus made on the recording medium such as a CR-ROM.

The template data storage means 10 may be variously modified.

In one modification of the template data storage means 10, template data of the structure shown in the following table is prepared, and the contour shape of the standard template can be expressed by generating a curve such as a spline curve on the basis of control points while referring to information on the coordinate train of the control points, whether the control points are on an edge, and the like.

TABLE 1 data structure of template

| 1) model number | femur (left), femur (right) |
| --- | --- |
| 2) size | #7, #8, #9, #10 |
| 3) direction | front , side |
| 4) contour | outer edge, inner edge |
| 5) reference line | centerline, bone head axis |
| 6) reference point | bone head fixing position; 0 mm, 5 mm, 10 mm |
| 7) the others | 1: material, weight, price, maker, scale |
|  | 2: notes |

Figure 9A:
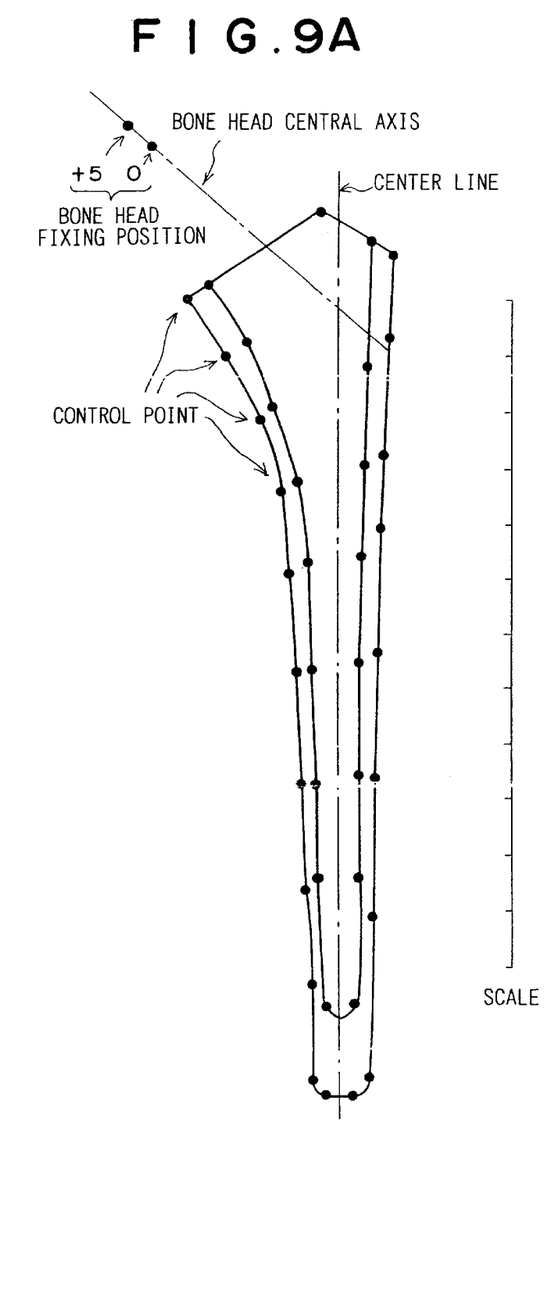
FIGS. 9A and 9B are views showing another example of the structure of template data.
Figure 9B:
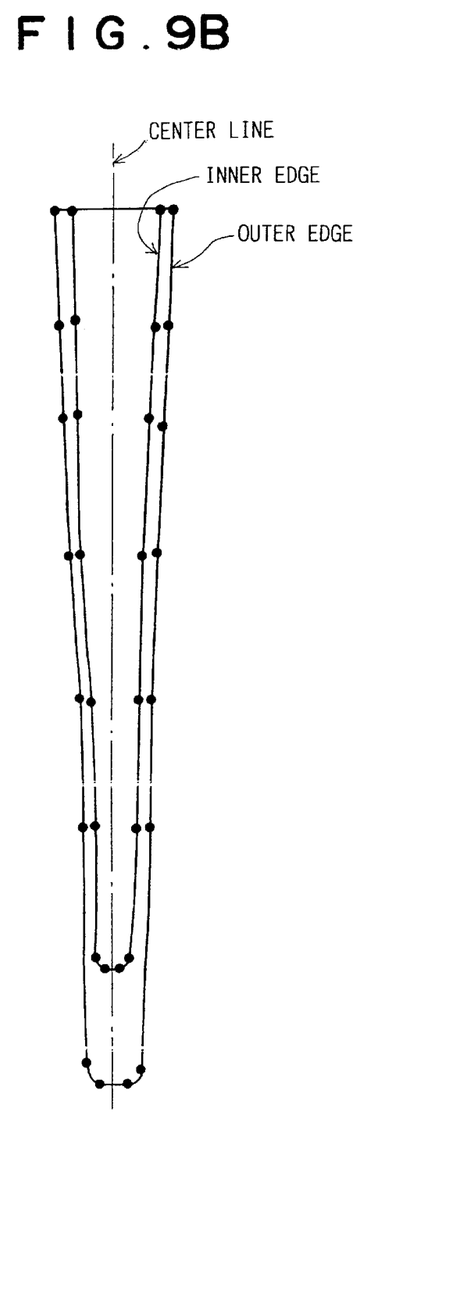

With this data structure, when the scale of an image of a template is varied in order to apply the image of the template to a displayed image of the bone to be replaced by artificial bone, the edge of the image of the template is smoothly displayed as shown in FIGS. 9A and 9B, whether the template is suitable for the bone can be easily checked.

When the degree of suitability is automatically calculated, simple digitization of the image of the template generates digitization errors. However, with the method described above, calculation errors can be suppressed.

What is claimed is:

1. An artificial bone template selection system comprising
   a template data storage means in which template data representing a plurality of templates representing a plurality of artificial bones of different shapes is stored,
   a bone shape measuring means which measures the shape of bone to be replaced by artificial bone on the basis of bone image data representing an image including the bone to be replaced by artificial bone, and
   a prospective template selection means which selects, as a prospective template, at least one template the shape of which substantially conforms to the shape of the bone to be replaced by artificial bone as measured by the bone shape measuring means out of the plurality of templates represented by the template data.

2. An artificial bone template selection system as defined in claim 1 further comprising
   a display means which displays the bone image representing the shape of the bone to be replaced by the artificial bone and an image of the prospective template(s) selected by the prospective template selection means and
   a display control means which causes the display means to display the bone image and the image of the prospective template superposed one on another.

3. An artificial bone template selection system as defined in claim 2 in which an image processing means which carries out image processing on at least one of the images displayed by the display means so that their shapes can be more clearly discriminated is provided, and
   the display control means causes the display means to display the image processed by the image processing means in the processed condition.

4. An artificial bone template selection system as defined in claim 1 further comprising an order information output means which outputs information for ordering artificial bone corresponding to the template selected by the prospective template selection means.

5. An artificial bone template selection system comprising
   a template data storage means in which template data representing a plurality of templates representing a plurality of artificial bones of different shapes is stored,
   a bone image display means which displays the bone image representing the shape of the bone to be replaced by the artificial bone,
   a feature point designating means which designates on the bone image displayed by the bone image display means a feature point representing the shape of the bone,
   a bone shape specifying means which specifies the shape of the bone on the basis of the feature point designated by the feature point designating means, and
   a prospective template selection means which selects, as a prospective template, at least one template the shape of which substantially conforms to the shape of the bone specified by the bone shape specifying means out of the plurality of templates represented by the template data.

6. An artificial bone template selection system as defined in claim 5 further comprising a display control means which causes the display means to display the bone image and the image of the prospective template superposed one on another.

7. An artificial bone template selection system as defined in claim 6 in which an image processing means which carries out image processing on at least one of the images displayed by the display means so that their shapes can be more clearly discriminated is provided, and
   the display control means causes the display means to display the image processed by the image processing means in the processed condition.

8. An artificial bone template selection system as defined in claim 5 further comprising an order information output means which outputs information for ordering artificial bone corresponding to the template selected by the prospective template selection means.

* * * * *